United States Patent
Sanders Millare et al.

(10) Patent No.: US 6,540,776 B2
(45) Date of Patent: Apr. 1, 2003

(54) SHEATH FOR A PROSTHESIS AND METHODS OF FORMING THE SAME

(75) Inventors: Deborra Sanders Millare, San Jose, CA (US); Steven Wu, Santa Clara, CA (US); Sameer Harish, Fremont, CA (US); Judy Guruwaiya, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 34 days.

(21) Appl. No.: 09/751,692

(22) Filed: Dec. 28, 2000

(65) Prior Publication Data

US 2002/0123788 A1 Sep. 5, 2002

(51) Int. Cl.[7] ............... A61F 2/06; A61F 9/00
(52) U.S. Cl. ........................ 623/1.15; 623/901
(58) Field of Search .................. 623/1.13, 1.14, 623/1.39–1.43, 1.44–1.48

(56) References Cited

U.S. PATENT DOCUMENTS

| | | | |
|---|---|---|---|
| 4,733,665 A | 3/1988 | Palmaz | 128/343 |
| 4,800,882 A | 1/1989 | Gianturco | 128/343 |
| 4,886,062 A | 12/1989 | Wiktor | 128/343 |
| 4,977,901 A | 12/1990 | Ofstead | 128/772 |
| 5,192,468 A * | 3/1993 | Coates et al. | 264/13 |
| 5,328,471 A | 7/1994 | Slepian | 604/101 |
| 5,464,650 A | 11/1995 | Berg et al. | 427/2.3 |
| 5,605,696 A | 2/1997 | Eury et al. | 424/423 |
| 5,628,730 A | 5/1997 | Shapland et al. | 604/21 |
| 5,649,977 A | 7/1997 | Campbell | 623/1 |
| 5,667,767 A | 9/1997 | Greff et al. | 424/9.411 |
| 5,670,558 A | 9/1997 | Onishi et al. | 523/112 |
| 5,700,286 A | 12/1997 | Tartaglia et al. | 623/1 |
| 5,716,981 A | 2/1998 | Hunter et al. | 514/449 |
| 5,800,392 A | 9/1998 | Racchini | 604/96 |
| 5,824,049 A | 10/1998 | Ragheb et al. | 623/1 |
| 5,830,178 A | 11/1998 | Jones et al. | 604/49 |
| 5,837,313 A | 11/1998 | Ding et al. | 427/2.21 |
| 5,851,508 A | 12/1998 | Greff et al. | 424/9.411 |
| 5,865,814 A | 2/1999 | Tuch | 604/265 |
| 5,873,904 A | 2/1999 | Ragheb et al. | 623/1 |
| 5,980,972 A | 11/1999 | Ding | 427/2.24 |
| 6,010,530 A | 1/2000 | Goicoechea | 623/1 |
| 6,015,541 A | 1/2000 | Greff et al. | 424/1.25 |
| 6,096,070 A | 8/2000 | Ragheb et al. | 623/1 |
| 6,139,573 A | 10/2000 | Sogard et al. | 623/1.13 |
| 6,153,252 A | 11/2000 | Hossainy et al. | 427/2.3 |
| 6,165,212 A | 12/2000 | Dereume et al. | |
| 6,258,121 B1 | 7/2001 | Yang et al. | 623/1.46 |
| 6,335,029 B1 * | 1/2002 | Kamath et al. | 424/422 |

FOREIGN PATENT DOCUMENTS

| | | | |
|---|---|---|---|
| EP | 0 665 023 | 8/1995 | |
| EP | 0 970 711 | 1/2000 | |
| JP | 11299901 | * 2/1999 | |
| WO | WO 91/12846 | 9/1991 | |
| WO | WO 97/45105 | 12/1997 | |
| WO | WO 99/63981 | 12/1999 | |
| WO | WO 00/02599 | 1/2000 | |
| WO | WO 00/12147 | 3/2000 | |
| WO | WO 00/38590 | 7/2000 | A61F/2/06 |
| WO | WO 00/38754 | 7/2000 | A61L/31/10 |
| WO | WO 00/42949 | 7/2000 | A61F/2/06 |
| WO | WO 00/56247 | 9/2000 | A61F/2/06 |
| WO | WO 00/57818 | 10/2000 | A61F/2/06 |
| WO | WO 00/64506 | 11/2000 | |
| WO | WO 00/71052 | 11/2000 | A61F/2/06 |
| WO | WO 01/01890 | 1/2001 | |
| WO | WO 01/45763 | 6/2001 | |

* cited by examiner

*Primary Examiner*—Corrine McDermott
*Assistant Examiner*—Hieu Phan
(74) *Attorney, Agent, or Firm*—Squire, Sanders & Dempsey LLP

(57) ABSTRACT

An implantable device or endoluminal prosthesis, such as a stent, having a sheath and a method of forming the sheath are provided. The sheath may be used for the delivery of an active ingredient. The sheath may have a selected pattern of interstices for allowing a fluid to seep through the sheath in the direction of the pattern created.

10 Claims, 3 Drawing Sheets

SHEATH FOR A PROSTHESIS AND METHODS OF FORMING THE SAME

BACKGROUND OF THE INVENTION

1. Field of the Invention

The invention relates to implantable devices or endoluminal prostheses, such as stents, and methods of forming a sheath on such devices.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially press against the atherosclerotic plaque of the lesion for remodeling of the vessel wall. The balloon is then deflated to a smaller profile to allow the catheter to be withdrawn from the patient's vasculature.

A problem associated with the above procedure includes formation of intimal flaps or torn arterial linings, which can collapse and occlude the conduit after the balloon is deflated. Vasospasms and recoil of the vessel wall also threaten vessel closure. Moreover, thrombosis and restenosis of the artery may develop over several months after the procedure, which may necessitate another angioplasty procedure or a surgical by-pass operation. To reduce the partial or total occlusion of the artery by the collapse of arterial lining and to reduce the chance of the development of thrombosis and restenosis, an expandable, intraluminal prosthesis, one example of which is a stent, is implanted in the lumen to maintain the vascular patency.

Stents act as scaffoldings, functioning to physically hold open and, if desired, to expand the wall of the passageway. Typically stents are capable of being compressed, so that they can be inserted through small cavities via catheters, and then expanded to a larger diameter once they are at the desired location. Examples in the patent literature disclosing stents that have been applied in PTCA procedures include U.S. Pat. No. 4,733,665 issued to Palmaz, U.S. Pat. No. 4,800,882 issued to Gianturco, and U.S. Pat. No. 4,886,062 issued to Wiktor. Mechanical intervention via stents has reduced the rate of restenosis as compared to balloon angioplasty. Yet, restenosis is still a significant clinical problem with rates ranging from 20–40%. When restenosis does occur in the stented segment, its treatment can be challenging, as clinical options are more limited as compared to lesions that were treated solely with a balloon.

Stents are used not only for mechanical intervention but also as vehicles for providing biological therapy. Biological therapy can be achieved by medicating the stents. Medicated stents provide for the local administration of a therapeutic substance at the diseased site. In order to provide an efficacious concentration to the treated site, systemic administration of such medication often produces adverse or even toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

Depending on the physiological mechanism targeted, the therapeutic substance may be required to be released at an efficacious concentration for an extended duration of time. Increasing the quantity of the therapeutic substance in the polymeric coating can lead to poor coating mechanical properties, inadequate coating adhesion, and overly rapid rate of release. Increasing the quantity of the polymeric compound by producing a thicker coating can perturb the geometrical and mechanical functionality of the stent, as well as limit the procedure for which the stent can be used.

It is desirable to increase the residence time of a substance at the site of implantation, at a therapeutically useful concentration, without the application of a thicker coating. It is also desirable to be able to increase the quantity of the therapeutic substance carried by the polymeric layer without perturbing the mechanical properties of the coating, such as adhesion of the polymer to the stent substrate.

SUMMARY OF THE INVENTION

The present invention provides a method of forming a sheath on a prosthesis, e.g., a stent. The method includes providing a prosthesis for implantation in a biological passageway. The prosthesis has a longitudinally extending central bore for allowing a fluid to travel through the prosthesis in the passageway and includes a plurality of interconnected struts separated by gaps. The method includes forming a sheath circumscribing at least a portion of the prosthesis. The sheath covers the gaps underlying the sheath. In one embodiment, the sheath contains an active ingredient. In other embodiments, the sheath contains radiopaque elements, radioactive isotopes, nucleic acids, or proteins. The method can further include removing a portion of the sheath positioned over some of the gaps to form a pattern of interstices dispersed between the struts for allowing a fluid that flows through the central bore to seep through the sheath.

Also provided is a stent. The stent includes a generally tubular structure having a plurality of interconnected struts. A sheath is disposed about an outer surface of the generally tubular structure. In addition, the stent includes a pattern of interstices disposed in the sheath, interspersed between the struts. The interstices allow a fluid to flow through the sheath.

Also provided is a method for increasing the amount of a polymeric coating, without increasing the thickness of the coating, for a stent having struts separated by gaps. The method includes applying a composition including a polymeric compound and a solvent to the stent. The method also includes removing the solvent from the composition applied to the stent to form a coating. The coating covers the struts and the gaps between the struts so as to increase the quantity of the polymeric material supported by the stent without increasing the thickness of the coating on the stent. The method can also include removing a portion of the coating deposited over at least one of the gaps to create an opening in the coating. The size of the opening is smaller than the size of the gap.

DETAILED DESCRIPTION OF THE EMBODIMENTS

Some of the various embodiments of the present invention are illustrated by FIGS. 1–4. The Figures have not been drawn to scale, and the size of the various regions have been over or under emphasized for illustrative purposes.

Examples of the Device

Figure 1:
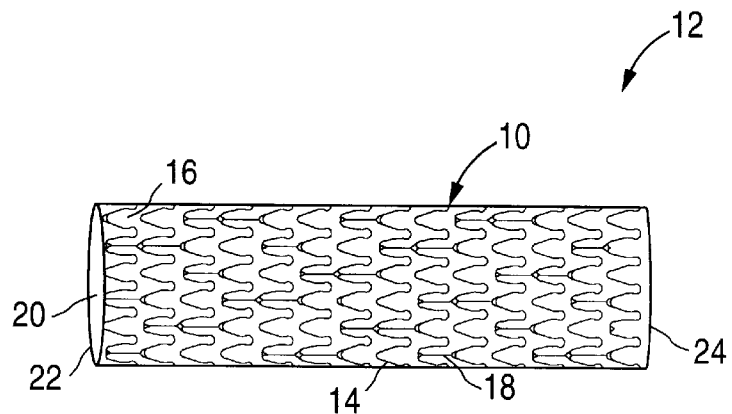
FIG. 1 illustrates a side view of an implantable device.

The device or prosthesis used in conjunction with the compositions described below may be any suitable device used for the release of an active ingredient or for the incorporation of radiopaque or radioactive materials, examples of which include self-expandable stents, balloon-expandable stents, grafts, and stent-grafts. Referring to FIG. 1, a body 10 of a device 12 is formed from a plurality of struts 14. Struts 14 are separated by gaps 16 and may be interconnected by connecting elements 18. Struts 14 can be connected in any suitable configuration and pattern. Body 10 is illustrated having an outer surface (tissue-contacting surface) and an inner surface. A hollow, central bore 20 extends longitudinally from a first end 22 to a second end 24 of body 10.

Device 12 can be made of a metallic material or an alloy such as, but not limited to, stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Device 12 made from bioabsorbable or biostable polymers could also be used with the embodiments of the present invention. A polymeric device should be compatible with the selected compositions.

Composition for Forming a Sheath

The embodiments of the composition for forming a sheath on the above-described device 12 are prepared by conventional methods wherein all components are combined, then blended. More particularly, in accordance with one embodiment, a predetermined amount of a polymeric compound is added to a predetermined amount of a mutually compatible solvent. The polymeric compound can be added to the solvent at ambient pressure and, if applicable, under anhydrous atmosphere. If necessary, gentle heating and stirring and/or mixing can be employed to effect dissolution of the polymer into the solvent, for example 12 hours in a water bath at about 60° C.

"Polymer," "poly," and "polymeric" are defined as compounds that are the product of a polymerization reaction and are inclusive of homopolymers, copolymers, terpolymers etc., including random, alternating, block, and graft variations thereof. The polymer chosen must be a polymer that is biocompatible. The polymer may be bioabsorbable or biostable. Bioabsorbable polymers that may be used include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid. In addition, biostable polymers with a relatively low chronic tissue response such as polyurethanes, silicones, and polyesters may be used, and other polymers may also be used if they can be dissolved and cured or polymerized on device 12 such as polyolefins, polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

Ethylene vinyl alcohol is functionally a very suitable choice of polymer. The copolymer adheres well to metal surfaces, such as stainless steel, and has illustrated the ability to expand with a stent without any significant detachment of the copolymer from the surface of the stent. Ethylene vinyl alcohol copolymer, commonly known by the generic name EVOH or by the trade name EVAL, refers to copolymers comprising residues of both ethylene and vinyl alcohol monomers. One of ordinary skill in the art understands that ethylene vinyl alcohol copolymer may also be a terpolymer so as to include small amounts of additional monomers, for example less than about five (5) mole percentage of styrenes, propylene, or other suitable monomers. In a useful embodiment, the copolymer comprises a mole percent of ethylene of from about 27% to about 47%. Typically, 44 mole percent ethylene is suitable. Ethylene vinyl alcohol copolymers are available commercially from companies such as Aldrich Chemical Company, Milwaukee, Wis., or EVAL Company of America, Lisle, Ill., or can be prepared by conventional polymerization procedures that are well known to one of ordinary skill in the art.

The solvent should be capable of placing the polymer into solution at the concentration desired in the composition. Examples of solvents include, but are not limited to, dimethylsulfoxide (DMSO), chloroform, acetone, water (buffered saline), xylene, acetone, methanol, ethanol, 1-propanol, tetrahydrofuran, 1-butanone, dimethylformamide, dimethylacetamide, cyclohexanone, and N-methyl pyrrolidinone. With the use of low ethylene content, e.g., 29 mol %, ethylene vinyl alcohol copolymer, a suitable solvent is iso-propylalcohol (IPA) admixed with water (e.g., 1:1).

By way of example, the polymer can comprise from about 15% to about 34%, more narrowly from about 20% to about 25% by weight of the total weight of the composition, and the solvent can comprise from about 66% to about 85%, more narrowly from about 75% to about 80% by weight of the total weight of the composition.

In another embodiment, sufficient amounts of an active ingredient are dispersed in the blended composition of the polymer and the solvent. The active ingredient may be in true solution or saturated in the blended composition. If the active ingredient is not completely soluble in the composition, operations including mixing, stirring, and/or agitation can be employed to effect homogeneity of the residues. The active ingredient may be added so that the dispersion is in fine particles. The mixing of the active ingredient can be conducted at ambient pressure, at room temperature, and if applicable in an anhydrous atmosphere, such that supersaturating the active ingredient is not desired.

The active ingredient may be any substance capable of exerting a therapeutic or prophylactic effect in the practice of the present invention. Examples of such active ingredients include antiproliferative, antineoplastic, antiinflammatory, antiplatelet, anticoagulant, antifibrin, antithrombin, antimitotic, antibiotic, and antioxidant substances as well as combinations thereof.

A suitable example of an antiproliferative substance is actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck); calcium channel blockers (such as Nifedipine), colchicine, fibroblast growth factor (FGF) antagonists, fish oil (omega 3-fatty acid), histamine antagonist, LOVASTATIN (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone. Exposure of the composition to the active ingredient is not permitted to adversely alter the active ingredient's composition or characteristic. Accordingly, the particular active ingredient is selected for mutual compatibility with the blended polymer-solvent composition.

The dosage or concentration of the active ingredient required to produce a favorable therapeutic effect should be less than the level at which the active ingredient produces toxic effects and greater than the level at which non-therapeutic results are obtained. The dosage or concentration of the active ingredient required can depend upon factors such as the particular circumstances of the patient; the nature of the trauma; the nature of the therapy desired; the time over which the ingredient administered resides at the treatment site; and if other bioactive substances are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

By way of example, the polymer can comprise from about 14% to about 33%, more narrowly from about 20% to about 25% by weight of the total weight of the composition, the solvent can comprise from about 33% to about 85%, more narrowly from about 50% to about 70% by weight of the total weight of the composition, and the active ingredient can comprise from about 1% to about 50%, more narrowly from about 10% to about 25% by weight of the total weight of the composition. More than 40% by weight of the active ingredient could adversely affect characteristics that are desirable in the polymeric coating, such as controlled release of the active ingredient. Selection of a specific weight ratio of the polymer and solvent is dependent on factors such as, but not limited to, the material from which the device is made, the geometrical structure of the device, and the type and amount of the active ingredient employed. The particular weight percentage of the active ingredient mixed within the composition depends on factors such as duration of the release, cumulative amount of release, and release rate that is desired.

In accordance with another embodiment, the polymeric composition includes radiopaque elements. Examples of radiopaque elements include, but are not limited to, gold, tantalum, and platinum. Sufficient amounts of radiopaque elements may be dispersed in the composition. By dispersed it is meant that the radiopaque elements are not present in the composition as agglomerates or flocs. In some compositions, certain elements will disperse with ordinary mixing. Otherwise, the elements can be dispersed in the composition by high shear processes such as ball mill, disc mill, sand mill, attritor, rotor stator mixer, or ultrasonication—all such high shear dispersion techniques being well known to one of ordinary skill in the art. Biocompatible dispersing agents in the form of surfactants, emulsifiers, or stablilizers may also be added to the composition to assist in dispersion.

In accordance with another embodiment, radioactive isotopes are present in the composition. An exemplary radioactive isotope is $P^{32}$. The radioactive isotopes should be dispersed in the blend, as defined above with reference to radiopaque elements.

Formation of an Optional Primer Layer

An optional primer layer can be formed on the outer surface of device 12 prior to the formation of the sheath. The presence of an active ingredient in a polymeric matrix typically interferes with the ability of the matrix to adhere effectively to the surface of the device. An increase in the quantity of the active ingredient reduces the effectiveness of the adhesion. High drug loadings of, for example, 10–40% by weight in the coating may significantly hinder the retention of the coating on the surface of the device. The primer layer serves as a functionally useful intermediary layer between the surface of the device and an active ingredient-containing sheath. The primer layer provides for an adhesive tie between the sheath and the device—which, in effect, would also allow for the quantity of the active ingredient in the sheath to be increased without compromising the ability of the sheath to be effectively contained on the device during delivery and, if applicable, expansion of the device.

To form an optional primer layer, the surfaces of device 12 should be clean and free from contaminants that may be introduced during manufacturing. However, the surfaces of device 12 require no particular surface treatment to retain the applied coating. Metallic surfaces of stents can be, for example, cleaned by an argon plasma process as is well known to one of ordinary skill in the art. Application of a primer composition, free from any active ingredients, can be by any conventional method, such as by spraying the primer composition onto device 12 or immersing device 12 in the primer composition. A hypotube or a mandrel can be placed within central bore 20 of device 12 prior to the application of the primer composition.

With the use of thermoplastic polymers such as, but not limited to, ethylene vinyl alcohol copolymer, polycaprolactone, poly(lactide-co-glycolide), and poly(hydroxybutyrate), the deposited primer composition should be exposed to a heat treatment at a temperature range greater than about the glass transition temperature ($T_g$) and less than about the melting temperature ($T_m$) of the selected polymer. Unexpected results have been discovered with treatment of the composition under this temperature range, specifically strong adhesion or bonding of the coating to the metallic surface of a stent. Device 12 should be exposed to the heat treatment for any suitable duration of time that will allow for the formation of the primer layer on the outer surface of device 12 and for the evaporation of the solvent employed. It is understood that essentially all of the solvent will be removed from the primer composition but traces or residues can remain blended with the polymer.

Table 1 lists the $T_g$ and $T_m$ for some of the polymers used in the embodiments of the primer layer. $T_g$ and $T_m$ of polymers are attainable by one of ordinary skill in the art. The cited exemplary temperature and time for exposure are provided by way of illustration and are not meant to be limiting.

TABLE 1

| Polymer | $T_g$ (° C.) | $T_m$ (° C.) | Exemplary Temperature (° C.) | Exemplary Duration of Time For Heating |
|---|---|---|---|---|
| EVOH | 55 | 165 | 140 | 4 hours |
| polycaprolactone | −60 | 60 | 50 | 2 hours |
| ethylene vinyl acetate (e.g., 33% vinyl acetate content) | 36 | 63 | 45 | 2 hours |
| Polyvinyl alcohol | 75–85* | 200–220* | 165 | 2 hours |

TABLE 1-continued

| Polymer | $T_g$ (° C.) | $T_m$ (° C.) | Exemplary Temperature (° C.) | Exemplary Duration of Time For Heating |
|---|---|---|---|---|

*Exact temperature depends on the degree of hydrolysis which is also known as the amount of residual acetate.

Forming a Sheath from the Composition

Figure 2:
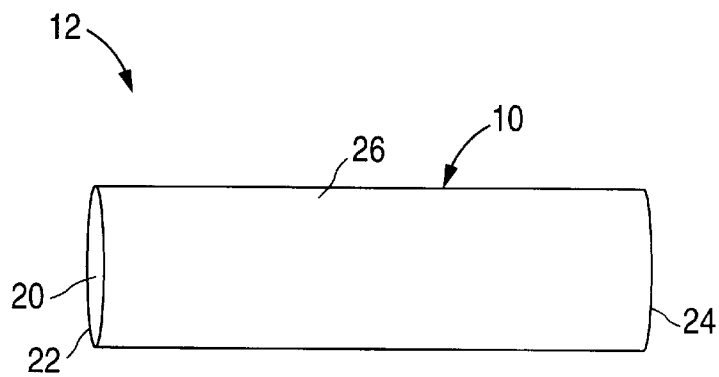
FIG. 2 illustrates the implantable device of FIG. 1 after a sheath has been formed about the outer surface thereof.

Referring now to FIG. 2, a sheath 26 is formed on device 12. To form sheath 26, the embodiments of the above-described composition, which may contain an active ingredient, can be applied on the outer surface or on the above-described primer layer, if used. The solvent may then be removed from the composition to form sheath 26.

Application of the composition can be accomplished by any conventional method, such as by spraying the composition onto device 12 or immersing device 12 in the composition. Such application methods are understood by one of ordinary skill in the art. The composition coats struts 14 as well as gaps 16 between struts 14.

In some embodiments, application of the composition is preceded by first placing a mandrel or hypotube within central bore 20 of device 12 such that a tight fit is achieved between the mandrel or hypotube and the inner surface of device 12. The composition may then be applied to device 12 having the mandrel or hypotube therein.

The solvent is removed from the composition by allowing the solvent to evaporate. The evaporation can be induced by heating device 12 at a predetermined temperature for a predetermined period of time. For example, the device can be heated at a temperature of about 60° C. for about 12 hours to about 24 hours. The heating can be conducted in an anhydrous atmosphere and at ambient pressure and should not exceed a temperature that would adversely affect the active ingredient. The heating can, alternatively, be conducted under a vacuum condition. It is understood that essentially all of the solvent will be removed from the composition but traces or residues can remain blended with the polymer. Upon removal of the solvent from the composition, sheath 26 is formed such that sheath 26 covers struts 14 as well as gaps 16 between struts 14.

As mentioned above, conventional coating methods coat the struts of a stent, leaving voids in the coating over the gaps between the struts. By forming sheath 26 to cover struts 14 as well as gaps 16 between struts 14, the present invention allows an increased amount of polymeric matrix to be present on device 12 without increasing the thickness of the coating. The amount of therapeutic substance, accordingly, is increased concomitantly.

Patterning the Sheath to Form Interstices Therein

Figure 3A:
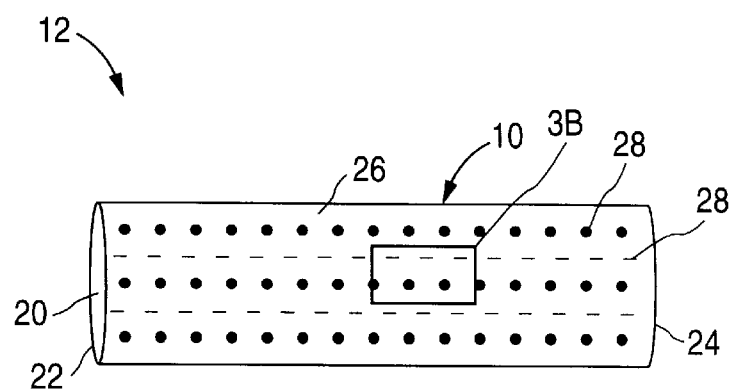
FIG. 3A illustrates the implantable device of FIG. 2 after a pattern of interstices has been created within the sheath.
Figure 3B:
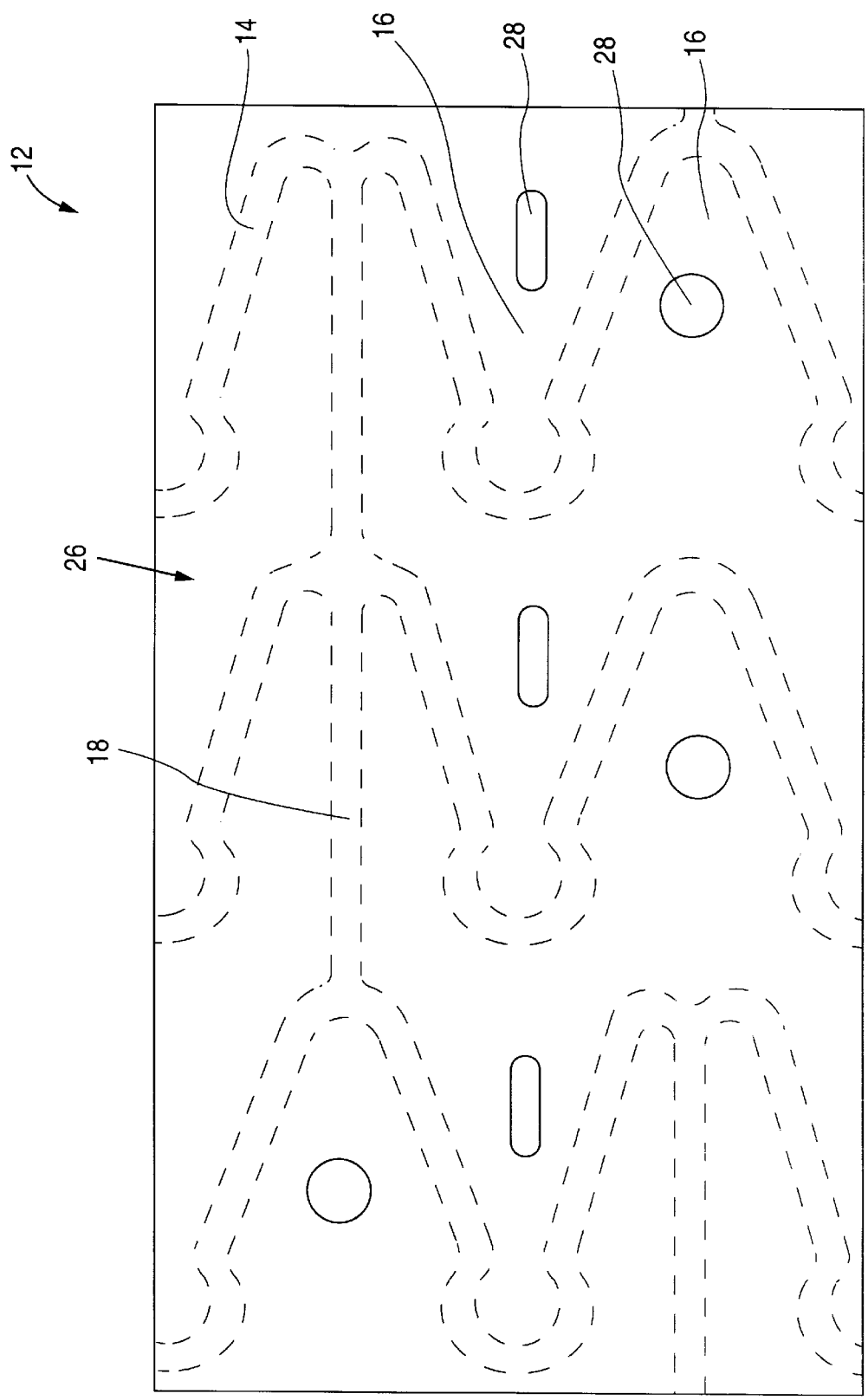
FIG. 3B illustrates an enlarged view of region 3B of the implantable device in FIG. 3A.

As illustrated in FIGS. 3A and 3B, sheath 26 is patterned such that portions of sheath 26 positioned over at least some of gaps 16 are removed to yield a pattern of interstices 28 dispersed between struts 14. Such patterning of sheath 26 may be accomplished, for example, by exposing designated portions of sheath 26 to the discharge of a laser, such as an excimer laser. Application of a laser discharge to form patterns can be performed by one of ordinary skill in the art.

Interstices 28 may be of any suitable size and shape and are typically smaller than the gap 16 in which they are created. Interstices 28 may be interspersed between struts 14 in any pattern. The pattern of interstices 28 created depends, in part, on the application for which device 12 is to be utilized.

Figure 4:
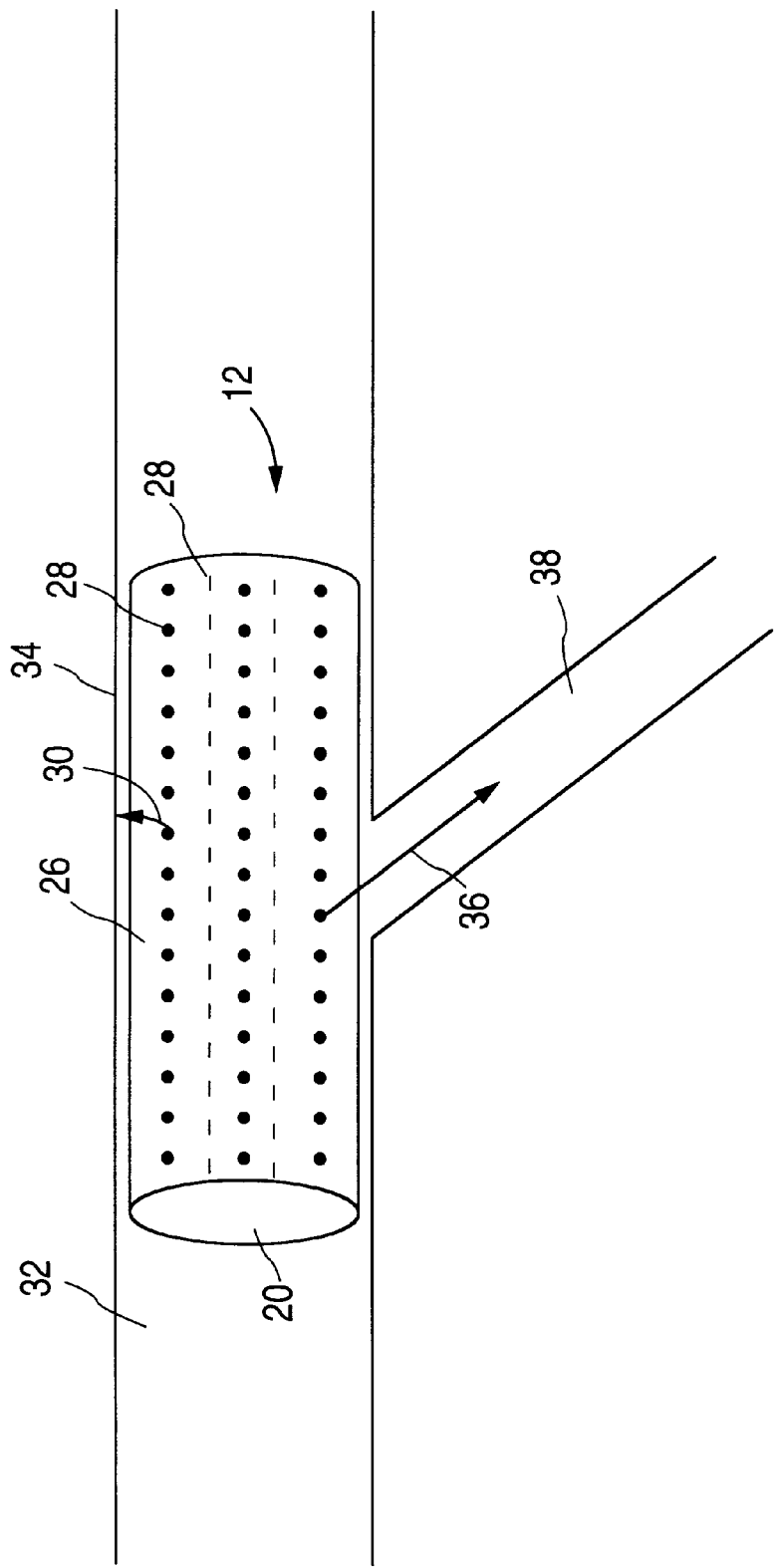
FIG. 4 illustrates exemplary paths of blood flow through interstices within the implantable device of FIG. 3A as employed in a blood vessel.

As illustrated in FIG. 4, interstices 28 allow a fluid, such as blood, which flows through central bore 20, to seep through sheath 26. Interstices 28 can be selectively patterned to direct the flow of blood in a selected direction, for example in a direction 30 to make contact with a vessel wall 34 of a targeted vessel 32. Such contact between blood and the vessel wall 34 may be required to allow vessel wall 34 to acquire essential nutrients from red blood cells. Alternatively, interstices 28 can be selectively patterned to direct the flow of blood in a direction 36 and into a side vessel 38. In this manner, the creation of interstices 28 allows branching side vessels 38 to remain patent during treatment of targeted vessel 32 with device 12.

Methods of Use

In accordance with the above-described methods, an active ingredient can be applied to a device, e.g., a stent, retained on the stent during delivery and expansion of the stent, and released at a desired control rate and for a predetermined duration of time at the site of implantation. A stent having the above-described patterned sheath is useful for a variety of medical procedures, including, by way of example, treatment of obstructions caused by tumors in bile ducts, esophagus, trachea/bronchi and other biological passageways. A stent having the above-described patterned sheath is particularly useful for treating occluded regions of blood vessels caused by abnormal or inappropriate migration and proliferation of smooth muscle cells, thrombosis, or restenosis. Stents may be placed in a wide array of blood vessels, both arteries and veins. Representative examples of sites include the iliac, renal, and coronary arteries.

Briefly, an angiogram is first performed to determine the appropriate positioning for stent therapy. Angiography is typically accomplished by injecting a radiopaque contrast agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described patterned sheath may then be expanded at the desired area of treatment. A post insertion angiogram may also be utilized to confirm appropriate positioning.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A method of forming a sheath for a prosthesis, comprising:

providing a prosthesis for implantation in a biological passageway, said prosthesis having a longitudinally extending central bore for allowing a fluid to travel through said prosthesis in said passageway, and said prosthesis having a plurality of interconnected struts separated by gaps;

forming a sheath circumscribing at least a portion of said prosthesis, wherein said sheath at least partially covers said gaps underlying said sheath;

removing a portion of said sheath positioned over some of said gaps to form a pattern of interstices dispersed between said struts for allowing a fluid that flows through said central bore to seep through said sheath; and wherein said forming a sheath comprises:
inserting a tube within said central bore of said prosthesis;
applying a composition comprising a solvent and a polymeric material dissolved in said solvent to said prosthesis;
allowing said solvent to evaporate from said composition to form said sheath; and
removing said tube from said central bore of said prosthesis, wherein said polymer remains at least partially over said gaps.

2. The method of claim 1, wherein said polymeric material is an ethylene vinyl alcohol copolymer.

3. The method of claim 1, wherein said removing is performed by applying a laser discharge to said portion of said sheath to form a preselected pattern of interstices.

4. The method of claim 1, wherein said sheath is impregnated with an active ingredient for the sustained release of said active ingredient when said prosthesis is implanted in a biological passageway.

5. The method of claim 4, wherein said active ingredient is selected from a group of antiproliferative, antineoplastic, antiinflammatory, antiplatelet, anticoagulant, antifibrin, antithrombin, antimitotic, antibiotic, antioxidant substances and combinations thereof.

6. The method of claim 1, wherein said sheath contains actinomycin D, docetaxel, or paclitaxel.

7. The method of claim 1, wherein the prosthesis is a balloon expandable or self-expandable stent.

8. A method of forming a sheath for a prosthesis, comprising:

providing a prosthesis for implantation in a biological passageway, said prosthesis having a longitudinally extending central bore for allowing a fluid to travel through said prosthesis in said passageway, and said prosthesis having a plurality of interconnected struts separated by gaps;

forming a sheath circumscribing at least a portion of said prosthesis, wherein said sheath at least partially covers said gaps underlying said sheath;

removing a portion of said sheath positioned over some of said gaps to form a pattern of interstices dispersed between said struts for allowing a fluid that flows through said central bore to seep through said sheath;

wherein said sheath contains a material selected from a group of therapeutic substances, radioactive isotopes and radiopaque elements.

9. The method of claim 8, wherein said therapeutic substance is a nucleic acid or a protein.

10. The method of claim 8, wherein the prosthesis is a balloon expandable or self-expandable stent.

* * * * *